(12) United States Patent
Ovalles et al.

(10) Patent No.: US 9,255,043 B2
(45) Date of Patent: Feb. 9, 2016

(54) LIQUID CRUDE HYDROCARBON COMPOSITION

(75) Inventors: Cesar Ovalles, Walnut Creek, CA (US); John Segerstrom, Oxnard, CA (US); Estrella Rogel, Orinda, CA (US); Curt Campbell, Contra Costa, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 28 days.

(21) Appl. No.: 13/199,453

(22) Filed: Aug. 31, 2011

(65) Prior Publication Data

US 2013/0048079 A1   Feb. 28, 2013

(51) Int. Cl.
| | |
|---|---|
| *C10G 53/06* | (2006.01) |
| *C10G 53/00* | (2006.01) |
| *C10C 3/00* | (2006.01) |
| *C07C 7/20* | (2006.01) |
| *C10L 1/14* | (2006.01) |
| *F17D 1/17* | (2006.01) |
| *C10L 1/16* | (2006.01) |
| *C10L 1/189* | (2006.01) |
| *C10L 1/198* | (2006.01) |
| *C10L 1/24* | (2006.01) |

(52) U.S. Cl.
CPC ... *C07C 7/20* (2013.01); *C10L 1/14* (2013.01); *C10L 1/143* (2013.01); *F17D 1/17* (2013.01); *C10G 2300/308* (2013.01); *C10L 1/1608* (2013.01); *C10L 1/1616* (2013.01); *C10L 1/189* (2013.01); *C10L 1/198* (2013.01); *C10L 1/2437* (2013.01); *C10L 2200/0453* (2013.01); *C10L 2230/14* (2013.01); *Y10T 137/0318* (2015.04)

(58) Field of Classification Search
CPC .... C10G 21/003; C10G 21/006; C10G 21/02; C10G 21/06; C10G 2300/308; C07C 7/20; F17D 1/17; C10L 1/143; C10L 1/14; C10L 1/1608; C10L 2230/14; C10L 1/198; C10L 1/189; C10L 2200/0453; C10L 1/2437; C10L 1/1616; Y10T 137/0318
USPC ............................................... 585/3; 137/1
See application file for complete search history.

(56) References Cited

U.S. PATENT DOCUMENTS

| | | | |
|---|---|---|---|
| 4,135,887 A | | 1/1979 | Rossi |
| 4,570,656 A | * | 2/1986 | Matlach et al. ................. 137/13 |
| 4,822,481 A | * | 4/1989 | Taylor ........................... 208/390 |
| 4,876,018 A | | 10/1989 | Karydas |
| 5,526,839 A | | 6/1996 | Padron |
| 5,925,233 A | | 7/1999 | Miller et al. |

(Continued)

OTHER PUBLICATIONS

The Written Opinion issued in counterpart Singapore Application No. 11201400259-T dated Mar. 20, 2105.

*Primary Examiner* — Pamela H Weiss
(74) *Attorney, Agent, or Firm* — M. Carmen & Associates, PLLC

(57) ABSTRACT

Disclosed is a liquid crude hydrocarbon composition containing (a) a liquid crude hydrocarbon having an API gravity of less than or equal to about 20; and (b) a minor amount of a blend comprising (i) one or more hydrocarbon-containing solvents having an aromatic content of at least about 10 wt. %; and (ii) one or more asphaltene modifiers selected from the group consisting of an aromatic sulfonic acid or salt thereof, an aliphatic sulfonic acid or salt thereof and an alkyl-substituted hydroxyaromatic carboxylic acid or salt thereof. Also disclosed is a method for transporting a liquid crude hydrocarbon having an API gravity of less than or equal to about 20.

10 Claims, 2 Drawing Sheets

(56) References Cited

U.S. PATENT DOCUMENTS

| | | |
|---|---|---|
| 6,048,904 A | 4/2000 | Wiehe et al. |
| 6,178,980 B1 | 1/2001 | Storm |
| 6,187,172 B1 | 2/2001 | Plummer |
| 6,488,724 B1 | 12/2002 | Hertel et al. |
| 7,183,452 B2 | 2/2007 | Campbell et al. |
| 8,123,930 B2 | 2/2012 | Cohrs et al. |
| 8,298,997 B2 | 10/2012 | Varadaraj et al. |
| 2004/0082823 A1 | 4/2004 | Kasaikina |
| 2004/0232051 A1 | 11/2004 | Varadaraj et al. |
| 2006/0014654 A1* | 1/2006 | Varadaraj et al. ............. 508/416 |
| 2013/6000749 | 1/2006 | Varadaraj et al. |
| 2046/0014654 | 1/2006 | Varadaraj et al. |
| 2006/0021907 A1 | 2/2006 | Varadaraj et al. |
| 2007/0295640 A1* | 12/2007 | Tan et al. ........................ 208/22 |
| 2009/0305933 A1* | 12/2009 | Stokes et al. .................. 510/188 |

\* cited by examiner

LIQUID CRUDE HYDROCARBON COMPOSITION

BACKGROUND OF THE INVENTION

1. Technical Field

The present invention generally relates to a liquid crude hydrocarbon composition and a method for its transportation.

2. Description of the Related Art

As world reserves of light, sweet crudes diminish and worldwide consumption of oil increases, refiners seek methods for extracting useful oils from heavier crude resources. Extensive reserves in the form of "heavy crudes" exist in a number of countries, including Western Canada, Venezuela, Russia, the United States, and elsewhere. For example, heavy or extra heavy crude oil can be found in the Orinoco Belt in Venezuela, the oil sands in Canada, and the Ugnu Reservoir in Northern Alaska. Alberta produces approximately two-thirds of Canada's oil and more than three-quarters of its natural gas. Nearly half of Alberta's oil is mined from vast oil sands, which are deposits of a heavy crude oil called bitumen. Alberta's oil sands represent the largest known deposits of bitumen in the world. The oil sands occur in three major areas of the province: the Athabasca River Valley in the northeast, the Peace River area in the north, and the Cold Lake region in east central Alberta.

The heavier crudes, which can include bitumens, heavy oils and tar sands, pose processing problems due to significantly higher concentration of contaminants such as sulfur and nitrogen as well as metals, most notably iron, nickel and vanadium. Bitumen is more costly to mine than conventional crude oil, which flows naturally or is pumped from the ground. This is because the thick black oil must be separated from the surrounding sand and water to produce a crude oil that can be further refined. The bitumen, which contrary to normal crude found in a deep reservoir, does not have the same light fractions normal crude. The bitumen thus consists of heavy molecules with a density exceeding 1.000 kg/dm$^3$ (less than 10 API) and a viscosity at reservoir conditions 1000 times higher than light crude. Because of the composition of the bitumen, it has to be upgraded before it can be refined in a refiner as light crude.

In addition, the large reserves of heavy or extra heavy crude oil are very viscous in their natural state. The viscous nature of these crude oils, however, makes it difficult to transport the oil in conventional pipelines to stations where it can be processed into useful end products. The origin of high viscosity in these oils has been attributed to high asphaltene content of the oils. Asphaltenes are organic heterocyclic macromolecules which occur in crude oils. Under normal reservoir conditions, asphaltenes are usually stabilized in the crude oil by maltenes and resins that are chemically compatible with asphaltenes, but that have lower molecular weight. Polar regions of the maltenes and resins surround the asphaltene while non-polar regions are attracted to the oil phase. Thus, these molecules act as surfactants and result in stabilizing the asphaltenes in the crude. However, changes in pressure, temperature or concentration of the crude oils can alter the stability of the dispersion and increase the tendency of the asphaltenes to agglomerate into larger particles. These agglomerates yield viscosities that are much higher than if the asphaltenes were not structured.

Generally, unwanted asphaltene precipitation is a concern to the petroleum industry due to, for example, plugging of an oil well or pipeline as well as stopping or decreasing oil production. Also, in downstream applications, asphaltenes are believed to be the source of coke during thermal upgrading processes thereby reducing and limiting yield of residue conversion. Accordingly, transporters and refiners of heavy crude oil have developed different techniques to improve the heavy crude oil's pumpability for transportation to a desired location.

One approach to transporting high asphaltene containing hydrocarbons is to add kerosene or other non-polar distillates. Kerosenes or distillates do not disperse asphaltene agglomerates; they merely dilute the agglomerates to obtain a lower viscosity of lesser extent than if the agglomerates were truly dispersed into individual molecules. However, adding kerosene or distillate in sufficient quantities to obtain the desired viscosity can be very costly, especially if the concentrations of the asphaltenes are high. Addition of kerosene or distillate in some cases can result in more agglomeration and can even cause precipitation of asphaltenes in crude oils.

Thus, it is generally advantageous to keep the asphaltenes in a stable suspension in the hydrocarbon liquid until well into the refining process. This not only increases the ultimate yield but also prevents or reduces the maintenance problems in the process and improves productivity from hydrocarbon formations. One solution has been to form oil-in-water emulsions. Oil-in-water emulsions exhibit greatly reduced viscosity which facilitates its transport through a pipeline. For example, U.S. Pat. No. 4,392,944 ("the '944 patent") discloses a stable oil-in-water emulsion of heavy crude oil and bitumen and subsequent breaking of the emulsion. The '944 patent discloses that the emulsion can be broken by conversion of the oil-in-water emulsion into a water-in-oil emulsion using calcium hydroxide (i.e., slaked lime or hydrated lime) and dewatering of the resulting water-in-oil emulsion.

Another example is U.S. Pat. No. 5,526,839 which discloses a method for forming a stable emulsion of a viscous crude hydrocarbon in an aqueous buffer solution, involving the steps of (a) providing a viscous crude hydrocarbon containing an inactive natural surfactant; (b) forming a solution of a buffer additive in an aqueous solution to provide a basic aqueous buffer solution, wherein the buffer additive activates the inactive natural surfactant from the viscous crude hydrocarbon; and (c) mixing the viscous crude hydrocarbon with the aqueous buffer solution at a rate sufficient to provide a stable emulsion of the viscous crude hydrocarbon in the aqueous buffer solution.

Another solution has been the use of dispersants to disassemble or break up the agglomerates of asphaltenes in the oil. For example, U.S. Pat. No. 6,187,172 discloses a method for dispersing asphaltenes in a liquid hydrocarbon by incorporating into the liquid hydrocarbon a sufficient concentration, e.g., about 0.1 to about 25 weight percent, of a hydrocarbon soluble asphaltene dispersant. U.S. Pat. No. 6,488,724 discloses the use of the combination of alkoxylated fatty amine compounds or fatty amine derivatives and organic metal salts as an effective additive for heavy oils, in particular with regard to emulsifying and/or dispersing asphaltenes, sludge and the like.

Accordingly, it would be desirable to provide improved methods and systems for processing and transporting asphaltene-containing liquid crude hydrocarbons that can be carried out in a simple, cost efficient manner.

SUMMARY OF THE INVENTION

In accordance with one embodiment of the present invention, there is provided a liquid crude hydrocarbon composition comprising:

(a) a liquid crude hydrocarbon having an API gravity of less than or equal to about 20; and (b) a minor amount of a blend comprising (i) one or more hydrocarbon-containing solvents having an aromatic content of at least about 10 wt. %; and (ii) one or more asphaltene modifiers selected from the group consisting of an aromatic sulfonic acid or salt thereof, an aliphatic sulfonic acid or salt thereof and an alkyl-substituted hydroxyaromatic carboxylic acid or salt thereof.

In accordance with a second embodiment of the present invention, there is provided a method for transporting a liquid crude hydrocarbon, the method comprising the steps of:

(a) providing a liquid crude hydrocarbon having an API gravity of less than or equal to about 20;

(b) providing a blend comprising (i) one or more hydrocarbon-containing solvents having an aromatic content of at least about 10 wt. %; and (ii) one or more asphaltene modifiers selected from the group consisting of an aromatic sulfonic acid or salt thereof, an aliphatic sulfonic acid or salt thereof and an alkyl-substituted hydroxyaromatic carboxylic acid or salt thereof;

(c) mixing a minor amount of the blend with the liquid crude hydrocarbon to obtain a liquid crude hydrocarbon composition; and (d) transporting the liquid crude hydrocarbon composition to a treatment facility or a transportation carrier.

In accordance with a third embodiment of the present invention, the use of a minor amount of a blend comprising (i) one or more hydrocarbon-containing solvents having an aromatic content of at least about 10 wt. %; and (ii) one or more asphaltene modifiers selected from the group consisting of an aromatic sulfonic acid or salt thereof, an aliphatic sulfonic acid or salt thereof and an alkyl-substituted hydroxyaromatic carboxylic acid or salt thereof, in a liquid crude hydrocarbon composition comprising a liquid crude hydrocarbon having an API gravity of less than or equal to about 20 for the purpose of transporting the liquid crude hydrocarbon composition to a treatment facility or a transportation carrier is provided.

The present invention combines a liquid crude hydrocarbon having an API gravity of less than or equal to about 20 with a minor amount of a blend comprising (i) one or more hydrocarbon-containing solvents having an aromatic content of at least about 10 wt. %; and (ii) one or more asphaltene modifiers selected from the group consisting of an aromatic sulfonic acid or salt thereof, an aliphatic sulfonic acid or salt thereof and an alkyl-substituted hydroxyaromatic carboxylic acid or salt thereof. The one or more hydrocarbon-containing solvents having an aromatic content of at least about 10 wt. % advantageously prevent or inhibit asphaltenes from precipitating from the resulting liquid crude hydrocarbon composition while the one or more of the asphaltene modifiers advantageously prevent or inhibit asphaltenes from agglomerating in the resulting liquid crude hydrocarbon composition. In this manner, the liquid crude hydrocarbon can be handled and transported, e.g., through a pipeline, in a simple, cost efficient manner. Further, the combination of the one or more hydrocarbon-containing solvents having an aromatic content of at least about 10 wt. % and one or more of the asphaltene modifiers can increase the conversion of heavy residue during thermal processing or hydroprocessing while also being capable of preventing sediment formation and fouling during downstream operations.

DETAILED DESCRIPTION OF THE PREFERRED EMBODIMENTS

Figure 1:
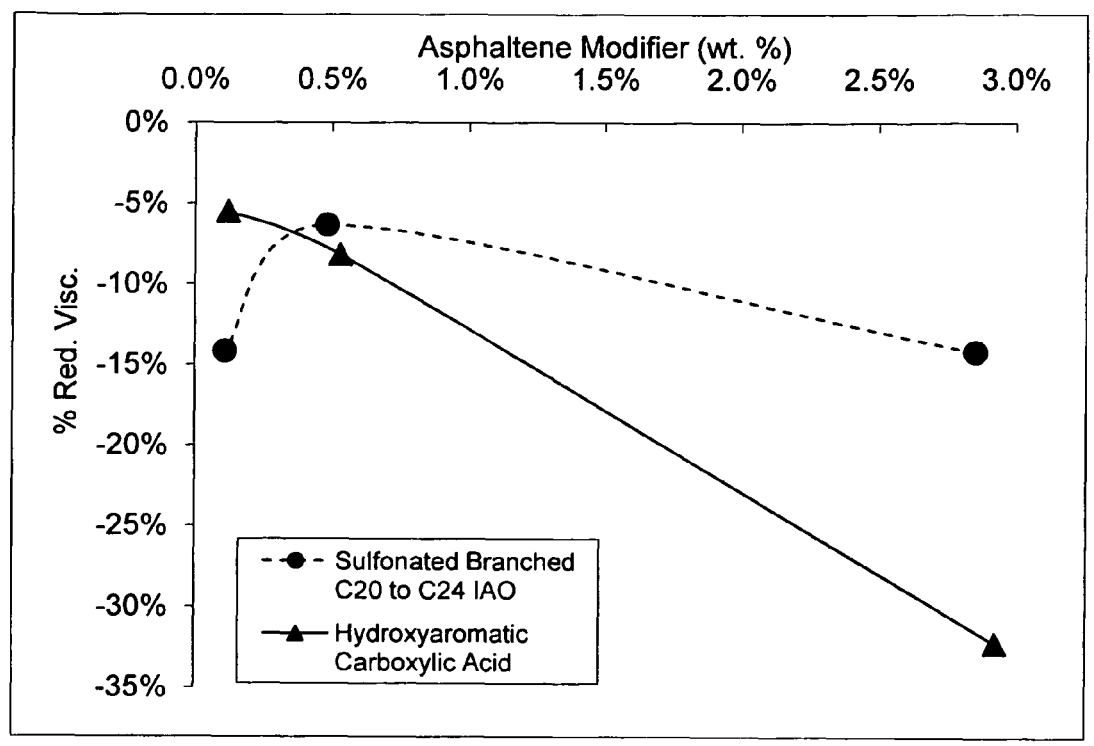
FIG. 1 shows viscosity reduction as a function of the concentration of asphaltene modifier in a liquid crude hydrocarbon composition containing a 75/25 wt. % ratio of an extra heavy crude oil and hydrocarbon-containing solvent/asphaltene modifier blend, respectively.

The present invention is directed to a liquid crude hydrocarbon composition comprising (a) a liquid crude hydrocarbon having an API gravity of less than or equal to about 20; and (b) a minor amount of a blend comprising (i) one or more hydrocarbon-containing solvents having an aromatic content of at least about 10 wt. %; and (ii) one or more asphaltene modifiers selected from the group consisting of an aromatic sulfonic acid, an aliphatic sulfonic acid and an alkali or alkaline earth metal salt of an alkyl-substituted hydroxyaromatic carboxylic acid.

In general, the liquid crude hydrocarbon having an API gravity of less than or equal to about 20 are asphaltene-containing liquid crude hydrocarbons. Asphaltenes, sometime also referred to as asphalthenes, are a mixed solubility class of compounds as opposed to a chemical class of compounds, generally solid in nature and comprise polynuclear aromatics present in the solution of smaller aromatics and resin molecules, and are also present in the crude oils and heavy fractions in varying quantities. Asphaltenes do not usually exist in all of the condensates or in light crude oils; however, they are present in relatively large quantities in heavy crude oils and petroleum fractions. Asphaltenes are insoluble components or fractions and their concentrations are defined as the amount of asphaltenes precipitated by addition of an n-paraffin solvent to the feedstock which are completely soluble in aromatic solvents, as prescribed in the Institute of Petroleum Method IP-143.

The source of the produced liquid crude hydrocarbon may be any source where a liquid crude hydrocarbon having an API gravity of less than or equal to about 20 may be obtained, produced, or the like. The source may be one or more producing wells in fluid communication with a subterranean oil reservoir. The producing well(s) may be under thermal recovery conditions, or the producing well(s) may be in a heavy oil field where the hydrocarbon crude or oil is being produced from a reservoir having a strong water-drive. Crude oil is any type of crude oil or petroleum and may also include liquefied coal oil, tar sand oil, oil sand oil, oil shale oil, Orinoco tar or mixtures thereof. The crude oil includes crude oil distillates, hydrocarbon oil residue obtained from crude oil distillation or mixtures thereof. In general, the liquid crude hydrocarbon having an API gravity of less than or equal to about 20 will have a viscosity of from about 100 to about 2,000,000 cSt at 40° C.

In one embodiment, a liquid crude hydrocarbon is a heavy crude oil. The term "heavy crude oil" as used herein refers to a crude oil having an API gravity less than or equal to about 20 and a viscosity greater than about 100 cSt at 40° C. An example of a heavy crude oil includes Hamaca bitumen crude oil. A heavy crude oil has a relatively high asphaltene content with a relatively low hydrogen/carbon ratio. In one embodiment, the heavy crude oil has an asphaltene content of no more than about 20 wt. %. In one embodiment, a heavy crude oil is a crude oil having an API gravity less than or equal to about 20 and a viscosity greater than about 100 cSt and no more than 2,000,000 cSt at 40° C. Viscosity measurements are determined herein according to ASTM D445.

In another embodiment, a liquid crude hydrocarbon is an extra heavy crude oil. The term "extra heavy crude oil" as used herein refers to a crude oil having an API gravity less than or equal to about 12 and a viscosity greater than about 300 cSt at 40° C. In one embodiment, an extra heavy crude oil is a crude oil having an API gravity less than or equal to about 12 and a viscosity greater than about 300 cSt and no more than 2,000,000 cSt at 40° C. In one embodiment, the extra heavy crude oil has an asphaltene content of no more than about 20 wt. %.

In accordance with the present invention, a minor amount of a blend comprising (i) one or more hydrocarbon-containing solvents having an aromatic content of at least about 10 wt. %; and (ii) one or more asphaltene modifiers selected from the group consisting of an aromatic sulfonic acid or salt thereof, an aliphatic sulfonic acid or salt thereof and an alkyl-substituted hydroxyaromatic carboxylic acid or salt thereof is added to the liquid crude hydrocarbon in order to reduce its viscosity. In one embodiment, a minor amount of the blend is an amount ordinarily ranging from about 10 to about 40 wt. %, based on the total weight of the liquid crude hydrocarbon composition. In one embodiment, a minor amount of the blend is an amount ranging from about 15 to about 35 wt. %, based on the total weight of the liquid crude hydrocarbon composition.

The one or more hydrocarbon-containing solvents having an aromatic content of at least about 10 wt. % are liquid and advantageously prevent or inhibit asphaltenes from precipitating from the resulting liquid crude hydrocarbon composition. Suitable one or more hydrocarbon-containing solvents (i) include hydrocarbon-containing solvents having an aromatic content of at least about 10 wt. %. In one embodiment, the one or more hydrocarbon-containing solvents include hydrocarbon-containing solvents having an aromatic content of at least about 20 wt. %. In one embodiment, the one or more hydrocarbon-containing solvents include hydrocarbon-containing solvents having an aromatic content of at least about 25 wt. %. In one embodiment, the one or more hydrocarbon-containing solvents include hydrocarbon-containing solvents having an aromatic content of at least about 40 wt. %. In one embodiment, the one or more hydrocarbon-containing solvents include hydrocarbon-containing solvents having an aromatic content of at least about 60 wt. %. The aromatic content is the value measured according to ASTM D 1319.

In one embodiment, the one or more hydrocarbon-containing solvent having an aromatic content of at least about 10 wt. % can be derived from highly aromatic refinery streams such as fluid catalytic cracking cycle oils, e.g., FCC Light Cycle Oil ("LCO"), Medium Cycle Oil ("MCO"), and Heavy Cycle Oil ("HCO"), thermally cracked distillates, and straight run distillates. These highly aromatic refinery streams include those in the jet, naphtha or diesel distillation ranges. These refinery streams generally have a boiling-range above about 200° F. and more typically have a boiling range between about 350° F. and about 750° F. In one embodiment, the one or more hydrocarbon-containing solvent having an aromatic content of at least about 10 wt. % is a refinery stream having a boiling-range from about 200° F. to about 750° F.

In one embodiment, the one or more hydrocarbon-containing solvent having an aromatic content of at least about 10 wt. % include, for example, benzene and naphthylene, as well as $C_1$ to $C_{20}$ alkyl-substituted benzenes such as isopropyl benzene, ethyl benzene, toluene, and $C_1$ to $C_{20}$ alkyl-substituted naphthylenes such as isopropyl naphthylene. Benzenes and naphthylenes containing multiple $C_1$ to $C_{20}$ alkyl substitutions, such as xylenes, may also be used.

In general, the one or more hydrocarbon-containing solvents having an aromatic content of at least about 10 wt. % are present in the blend in a concentration ranging from about 95 to about 99.999 wt. %, based on the total weight of the blend. In one embodiment, the one or more hydrocarbon-containing solvents having an aromatic content of at least about 10 wt. % are present in the blend in a concentration ranging from about 99.9 to about 99.999 wt. %, based on the total weight of the blend.

The blend further contains one or more asphaltene modifiers selected from the group consisting of an aromatic sulfonic acid or salt thereof, an aliphatic sulfonic acid or salt thereof and an alkyl-substituted hydroxyaromatic carboxylic acid or salt thereof. The one or more of the asphaltene modifiers advantageously prevent or inhibit asphaltenes from agglomerating in the resulting liquid crude hydrocarbon composition. In addition, the one or more of the asphaltene modifiers advantageously reduce the viscosity of the liquid crude hydrocarbon composition by at least 3% as compared to the viscosity of the liquid crude hydrocarbon having an API gravity of less than or equal to about 20 combined with the one or more hydrocarbon-containing solvents. By reducing the viscosity of the liquid crude hydrocarbon composition, lower energy is required to transport the liquid crude hydrocarbon composition thereby resulting in a reduction in operating expenses. In one embodiment, the viscosity of the resulting liquid crude hydrocarbon composition is no more than about 200 cSt at 40° C. In another embodiment, the viscosity of the resulting liquid crude hydrocarbon composition is no more than about 150 cSt at 40° C. In one embodiment, the viscosity of the resulting liquid crude hydrocarbon composition is from about 2 to about 200 cSt at 40° C. In another embodiment, the viscosity of the resulting liquid crude hydrocarbon composition is from about 2 to about 150 cSt at 40° C.

In one embodiment, the asphaltene modifier is one or more aromatic sulfonic acids or salts thereof. The aromatic sulfonic acids or salts thereof include alkyl aromatic sulfonic acids or salts thereof obtained by the alkylation of an aromatic compound. The alkyl aromatic is then sulfonated to form an alkyl aromatic sulfonic acid. If desired the alkyl aromatic sulfonic acid can be neutralized with caustic to obtain a sodium alkyl aromatic sulfonate compound.

At least one aromatic compound or a mixture of aromatic compounds may be used to form the aromatic sulfonic acid or salt thereof. Suitable aromatic compounds or the aromatic compound mixture comprise at least one of monocyclic aromatics, such as benzene, toluene, xylene, cumene or mixtures thereof. In one embodiment, the at least one aromatic compound or aromatic compound mixture is xylene, including all isomers (i.e., meta-, ortho- and para-), and mixtures thereof. In one preferred embodiment, the at least one aromatic compound is ortho-xylene.

The at least one aromatic compound or the mixture of aromatic compounds is commercially available or may be prepared by methods that are well known in the art.

As noted above, the aromatic compound may be alkylated to form an alkyl aromatic compound. The alkylating agent employed to alkylate the aromatic compound may be derived from a variety of sources. Such sources include the normal alpha olefins, linear alpha olefins, isomerized linear alpha olefins, dimerized and oligomerized olefins, and olefins derived from olefin metathesis. The olefin may be a single carbon number olefin, or it may be a mixture of linear olefins, a mixture of isomerized linear olefins, a mixture of branched olefins, a mixture of partially branched olefins, or a mixture of any of the foregoing. Another source from which the olefins may be derived is through cracking of petroleum or Fischer-Tropsch wax. The Fischer-Tropsch wax may be hydrotreated prior to cracking. Other commercial sources include olefins derived from paraffin dehydrogenation and oligomerization of ethylene and other olefins, methanol-to-olefin processes (methanol cracker) and the like.

The olefins may selected from olefins with carbon numbers ranging from about 8 carbon atoms to about 60 carbon atoms. In one embodiment, the olefins are selected from olefins with carbon numbers ranging from about 10 to about 50 carbon atoms. In one embodiment, the olefins are selected from olefins with carbon numbers ranging from about 12 to about 40 carbon atoms.

In another embodiment, the olefin or the mixture of olefins is selected from linear alpha olefins or isomerized olefins containing from about 8 to about 60 carbon atoms. In one embodiment, the mixture of olefins is selected from linear alpha olefins or isomerized olefins containing from about 10 to about 50 carbon atoms. In one embodiment, the mixture of olefins is selected from linear alpha olefins or isomerized olefins containing from about 12 to about 40 carbon atoms.

In one embodiment, the mixture of branched olefins is selected from polyolefins which may be derived from $C_3$ or higher monoolefins (e.g., propylene oligomers, butylenes oligomers, or co-oligomers etc.). In one embodiment, the mixture of branched olefins is either propylene oligomers or butylenes oligomers or mixtures thereof.

The linear olefins that may be used for the alkylation reaction may be one or a mixture of normal alpha olefins selected from olefins having from about 8 to about 60 carbon atoms per molecule. In one embodiment, the normal alpha olefin is selected from olefins having from about 10 to about 50 carbon atoms per molecule. In one embodiment, the normal alpha olefin is selected from olefins having from about 12 to about 40 carbon atoms per molecule.

In one embodiment, the aromatic compound is alkylated with a mixture of normal alpha olefins containing from $C_8$ to $C_{60}$ carbon atoms. In one embodiment, the aromatic compound is alkylated with a mixture of normal alpha olefins containing from $C_{10}$ to $C_{50}$ carbon atoms. In another embodiment, the aromatic compound is alkylated with a mixture of normal alpha olefins containing from $C_{12}$ to $C_{40}$ carbon atoms to yield an aromatic alkylate.

The normal alpha olefins employed to make the alkylaromatic sulfonic acid or salt thereof are commercially available or may be prepared by methods that are well known in the art.

In one embodiment, the normal alpha olefins are isomerized using a solid or a liquid acid catalyst. A solid catalyst preferably has at least one metal oxide and an average pore size of less than 5.5 angstroms. In one embodiment, the solid catalyst is a molecular sieve with a one-dimensional pore system, such as SM-3, MAPO-11, SAPO-11, SSZ-32, ZSM-23, MAPO-39, SAPO-39, ZSM-22 or SSZ-20. Other possible acidic solid catalysts useful for isomerization include ZSM-35, SUZ-4, NU-23, NU-87 and natural or synthetic ferrierites. These molecular sieves are well known in the art and are discussed in Rosemarie Szostak's Handbook of Molecular Sieves (New York, Van Nostrand Reinhold, 1992) which is herein incorporated by reference for all purposes. A liquid type of isomerization catalyst that can be used is iron pentacarbonyl ($Fe(CO)_5$).

The process for isomerization of normal alpha olefins may be carried out in batch or continuous mode. The process temperatures may range from about 50° C. to about 250° C. In the batch mode, a typical method used is a stirred autoclave or glass flask, which may be heated to the desired reaction temperature. A continuous process is most efficiently carried out in a fixed bed process. Space rates in a fixed bed process can range from about 0.1 to about 10 or more weight hourly space velocity.

In a fixed bed process, the isomerization catalyst is charged to the reactor and activated or dried at a temperature of at least 125° C. under vacuum or flowing inert, dry gas. After activation, the temperature of the isomerization catalyst is adjusted to the desired reaction temperature and a flow of the olefin is introduced into the reactor. The reactor effluent containing the partially-branched, isomerized olefins is collected. The resulting partially-branched, isomerized olefins contain a different olefin distribution (i.e., alpha olefin, beta olefin; internal olefin, tri-substituted olefin, and vinylidene olefin) and branching content than that of the unisomerized olefin and conditions are selected in order to obtain the desired olefin distribution and the degree of branching.

Typically, the alkylated aromatic compound may be prepared using a Bronsted acid catalyst, a Lewis acid catalyst, or solid acidic catalysts.

The Bronsted acid catalyst may be selected from a group comprising hydrochloric acid, hydrofluoric acid, hydrobromic acid, sulfuric acid, perchloric acid, trifluoromethane sulfonic acid, fluorosulfonic acid, and nitric acid and the like. Preferably, the Bronsted acid catalyst is hydrofluoric acid.

The Lewis acid catalyst may be selected from the group of Lewis acids comprising aluminum trichloride, aluminum tribromide, aluminum triiodide, boron trifluoride, boron tribromide, boron triiodide and the like. In one embodiment, the Lewis acid catalyst is aluminum trichloride.

The solid acidic catalysts may be selected from a group comprising zeolites, acid clays, and/or silica-alumina. An eligible solid catalyst is a cation exchange resin in its acid form, for example, crosslinked sulfonic acid catalyst. The catalyst may be a molecular sieve. Eligible molecular sieves are silica-aluminophosphate molecular sieves or metal silica-aluminophosphate molecular sieves, in which the metal may be, for example, iron, cobalt or nickel. Other suitable examples of solid acidic catalysts are disclosed in U.S. Pat. No. 7,183,452, which is herein incorporated by reference.

The Bronsted acid catalyst may be regenerated after it becomes deactivated (i.e., the catalyst has lost all or some portion of its catalytic activity). Methods that are well known in the art may be used to regenerate the acid catalyst, for example, hydrofluoric acid.

The alkylation technologies used to produce the alkylaromatic will include Bronsted and/or Lewis acids as well as solid acid catalysts utilized in a batch, semi-batch or continuous process operating at between from about 0 to about 300° C.

The acid catalyst may be recycled when used in a continuous process. The acid catalyst may be recycled or regenerated when used in a batch process or a continuous process.

In one embodiment, the alkylation process is carried out by reacting a first amount of at least one aromatic compound or a mixture of aromatic compounds with a first amount of a mixture of olefin compounds in the presence of a Bronsted acid catalyst, such as hydrofluoric acid, in a first reactor in which agitation is maintained, thereby producing a first reaction mixture. The resulting first reaction mixture is held in a first alkylation zone under alkylation conditions for a time sufficient to convert the olefin to aromatic alkylate (i.e., a first reaction product). After a desired time, the first reaction product is removed from the alkylation zone and fed to a second reactor wherein the first reaction product is reacted with an additional amount of at least one aromatic compound or a mixture of aromatic compounds and an additional amount of acid catalyst and, optionally, with an additional amount of a mixture of olefin compounds wherein agitation is maintained. A second reaction mixture results and is held in a second alkylation zone under alkylation conditions for a time sufficient to convert the olefin to aromatic alkylate (i.e., a second reaction product). The second reaction product is fed to a liquid-liquid separator to allow hydrocarbon (i.e., organic) products to separate from the acid catalyst. The acid catalyst may be recycled to the reactor(s) in a closed loop cycle. The hydrocarbon product is further treated to remove excess unreacted aromatic compounds and, optionally, olefinic compounds from the desired alkylate product. The excess aromatic compounds may also be recycled to the reactor(s).

In another embodiment, the reaction takes place in more than two reactors which are located in series. Instead of feeding the second reaction product to a liquid-liquid separator, the second reaction product is fed to a third reactor wherein the second reaction product is reacted with an additional amount of at least one aromatic compound or a mixture of aromatic compounds and an additional amount of acid catalyst and, optionally, with an additional amount of a mixture of olefin compounds wherein agitation is maintained. A third reaction mixture results and is held in a third alkylation zone under alkylation conditions for a time sufficient to convert the olefin to aromatic alkylate (i.e., a third reaction product). The reactions take place in as many reactors as necessary to obtain the desired alkylated aromatic reaction product.

The total charge mole ratio of Bronsted acid catalyst to the olefin compounds is about 0.1 to about 1 for the combined reactors. Preferably, the charge mole ratio of Bronsted acid catalyst to the olefin compounds is no more than about 0.7 to about 1 in the first reactor and no less than about 0.3 to about 1 in the second reactor.

The total charge mole ratio of the aromatic compound to the olefin compounds is about 7.5:1 to about 1:1 for the combined reactors. Preferably, the charge mole ratio of the aromatic compound to the olefin compounds is no less than about 1.4:1 to about 1:1 in the first reactor and is no more than about 6.1:1 to about 1:1 in the second reactor.

Many types of reactor configurations may be used for the reactor zone. These include, but are not limited to, batch and continuous stirred tank reactors, reactor riser configurations, ebulating bed reactors, and other reactor configurations that are well known in the art. Many such reactors are known to those skilled in the art and are suitable for the alkylation reaction. Agitation is critical for the alkylation reaction and can be provided by rotating impellers, with or without baffles, static mixers, kinetic mixing in risers, or any other agitation devices that are well known in the art. The alkylation process may be carried out at temperatures from about 0° C. to about 100° C. The process is carried out under sufficient pressure that a substantial portion of the feed components remain in the liquid phase. Typically, a pressure of 0 to 150 psig is satisfactory to maintain feed and products in the liquid phase.

The residence time in the reactor is a time that is sufficient to convert a substantial portion of the olefin to alkylate product. The time required is from about 30 seconds to about 30 minutes. A more precise residence time may be determined by those skilled in the art using batch stirred tank reactors to measure the kinetics of the alkylation process.

The at least one aromatic compound or mixture of aromatic compounds and the olefin compounds may be injected separately into the reaction zone or may be mixed prior to injection. Both single and multiple reaction zones may be used with the injection of the aromatic compounds and the olefin compounds into one, several, or all reaction zones. The reaction zones need not be maintained at the same process conditions. The hydrocarbon feed for the alkylation process may comprise a mixture of aromatic compounds and olefin compounds in which the molar ratio of aromatic compounds to olefins is from about 0.5:1 to about 50:1 or more. In the case where the molar ratio of aromatic compounds to olefin is >1.0 to 1, there is an excess amount of aromatic compounds present. Preferably an excess of aromatic compounds is used to increase reaction rate and improve product selectivity. When excess aromatic compounds are used, the excess unreacted aromatic in the reactor effluent can be separated, e.g. by distillation, and recycled to the reactor.

In one embodiment, the alkyl aromatic is made by the alkylation of ortho-xylene which produces an alkylate containing several isomers, but in which at least about 90 wt. % of the alkylate is the 1, 3, 4-ring attachment structure, having about 40 to about 60 wt. % 2-alkyl attachment to the aromatic ring (i.e., wherein the longest alkyl chain is attached to the aromatic ring at the 2-position on the alkyl chain), or having about 45 to about 55 wt. % 2-alkyl attachment or having about 50 wt. % 2-alkyl attachment to the aromatic ring. In one embodiment, the alkylate will contain from about 1 to about 20 wt. % dialkylate species. In one embodiment, the alkylate will contain less than about 10 wt % dialkylate species. In one embodiment, at least about 95 wt. % and most preferred about 98 wt. % of the alkylate contains the 1, 3, 4-ring attachment structure. Upon sulfonation of the alkylate, a mixture of alkyl aromatic sulfonic acid isomers are formed such as 2-alkyl-4, 5-dimethyl benzene sulfonic acid isomer where the amount of this sulfonic acid isomer is present, for example, in an amount of from about 1 to about 90 wt. %, or in an amount of from about 10 to about 80 wt. % or in amount of at least about 70 wt. %.

Once the alkyl aromatic product is obtained as described above, it is further reacted to form an alkyl aromatic sulfonic acid, which can then be neutralized to the corresponding sulfonate. Sulfonation of the alkyl aromatic compound may be performed by any method known to one of ordinary skill in the art. The sulfonation reaction is typically carried out in a continuous falling film tubular reactor maintained at about 45° C. to about 75° C. The alkyl aromatic compound is placed in the reactor along with sulfur trioxide diluted with air thereby producing an alkylaryl sulfonic acid. Other sulfonation reagents, such as sulfuric acid, chlorosulfonic acid or sulfamic acid may also be employed. In one embodiment, the alkyl aromatic compound is sulfonated with sulfur trioxide diluted with air. The charge mole ratio of sulfur trioxide to alkylate is maintained at about 0.8 to about 1.1:1.

If desired, neutralization of the alkyl aromatic sulfonic acid may be carried out in a continuous or batch process by any method known to a person skilled in the art to produce alkyl aromatic sulfonates. Typically, an alkyl aromatic sulfonic acid is neutralized with a source of alkali or alkaline earth metal or ammonia, thereby producing an alkyl aromatic sulfonate. Non-limiting examples of suitable alkali metals include lithium, sodium, potassium, rubidium, and cesium. In one embodiment, a suitable alkali metal includes sodium and potassium. In another embodiment, a suitable alkali metal is sodium. Non-limiting examples of suitable alkaline earth metals include calcium, barium, magnesium, or strontium and the like. In one embodiment, a suitable alkaline earth metal is calcium. In one embodiment, the source is an alkali metal base such as an alkali metal hydroxide, e.g., sodium hydroxide or potassium hydroxide.

In one embodiment, the one or more asphaltene modifiers is one or more aliphatic sulfonic acids or salts thereof. In general, the aliphatic sulfonic acids are prepared by sulfonating an aliphatic compound. In one embodiment, the aliphatic compound can be a $C_2$ to $C_{80}$ aliphatic compound. In one embodiment, the aliphatic compound can be a $C_{10}$ to $C_{80}$ aliphatic compound. In one embodiment, the aliphatic compound can be a $C_{20}$ to $C_{60}$ aliphatic compound.

The aliphatic compound is typically an olefin derived from a variety of sources, including, by way of example, normal alpha olefins, linear alpha olefins, isomerized linear alpha olefins, dimerized and oligomerized olefins, and olefins derived from olefin metathesis. The olefin may be a single carbon number olefin, or it may be a mixture of linear olefins, a mixture of isomerized linear olefins, a mixture of branched olefins, a mixture of partially branched olefins, or a mixture of any of the foregoing. Another source from which the olefins may be derived is through cracking of petroleum or Fischer-Tropsch wax. The Fischer-Tropsch wax may be hydrotreated prior to cracking. Other commercial sources include olefins derived from paraffin dehydrogenation and oligomerization of ethylene and other olefins, methanol-to-olefin processes (methanol cracker) and the like.

The olefins may selected from olefins with carbon numbers ranging from about 8 carbon atoms to about 60 carbon atoms. In one embodiment, the olefins are selected from olefins with carbon numbers ranging from 10 to about 50 carbon atoms. In one embodiment, the olefins are selected from olefins with carbon numbers ranging from about 12 to about 40 carbon atoms. In one embodiment, the olefins are selected from olefins with carbon numbers ranging from about 18 to about 28 carbon atoms.

In another embodiment, the olefin or the mixture of olefins is selected from linear alpha olefins or isomerized olefins containing from about 8 to about 60 carbon atoms. In one embodiment, the mixture of olefins is selected from linear alpha olefins or isomerized olefins containing from about 10 to about 50 carbon atoms. In one embodiment, the mixture of olefins is selected from linear alpha olefins or isomerized olefins containing from about 12 to about 40 carbon atoms. In one embodiment, the olefins are selected from olefins with carbon numbers ranging from about 18 to about 28 carbon atoms.

In one embodiment, the mixture of branched olefins is selected from polyolefins which may be derived from $C_3$ or higher monoolefins (e.g., propylene oligomers, butylenes oligomers, or co-oligomers etc.). In one embodiment, the mixture of branched olefins is either propylene oligomers or butylenes oligomers or mixtures thereof.

The linear olefins that may be used as the aliphatic group may be one or a mixture of normal alpha olefins selected from olefins having from about 8 to about 60 carbon atoms per molecule. In one embodiment, the normal alpha olefin is selected from olefins having from about 10 to about 50 carbon atoms per molecule. In one embodiment, the normal alpha olefin is selected from olefins having from about 12 to about 40 carbon atoms per molecule. In one embodiment, the olefins are selected from olefins with carbon numbers ranging from about 18 to about 28 carbon atoms.

The normal alpha olefins employed as the aliphatic compound are commercially available or may be prepared by methods that are well known in the art.

Methods of isomerizing olefins are known and discussed above. Persons skilled in the art are able to choose isomerization conditions under which particular levels of isomerization may be achieved. Specifically, the level of isomerization is typically characterized by the amount of alpha olefins and the level of branching in a particular olefin sample or mixture. The amount of alpha olefin and the level of branching can in turn be determined using various conventional methods, including, for example, Fourrier Transformed Intra Red (FTIR) spectroscopy. In atypical FTIR spectroscopy method, the level (or percentage) of alpha olefins can be measured by following the absorbance of a particular sample at 910 $cm^{-1}$ and comparing it to the 910 $cm^{-1}$ absorbance of calibration samples with known alpha olefin levels. The level (or percentage) of alpha olefin in the calibration samples can be obtained, for example, from $^{13}C$ quantitative nuclear magnetic resonance (NMR) spectroscopy according to known protocols.

The percentage of branching can also be measured by FTIR spectroscopy by following the absorbance of a sample at 1378 $cm^{-1}$. This absorbance corresponds to the extent of deformation vibration of methyl groups. The absorbance of an isomerized olefin sample is then compared to the 1378 $cm^{-1}$ absorbance of a set of calibration samples with known branching levels. Typically, a particular olefin mix to be tested is first hydrogenated, converting the unbranched portion to n-alkanes arid the branched portion to branched alkanes. Gas chromatography is then used to distinguish the unbranched n-alkanes from the branched alkanes, the proportion of which correlates to the percent branching level in that olefin mix.

Sulfonation of the aliphatic compound may be performed by any method known to one of ordinary skill in the art to obtain an aliphatic sulfonic acid. The sulfonation reaction is typically carried out in a continuous falling film tubular reactor maintained at about 45° C. to about 75° C. The aliphatic compound is placed in the reactor along with, for example, sulfur trioxide diluted with air thereby producing an aliphatic sulfonic acid. Other sulfonation reagents, such as sulfuric acid, chlorosulfonic acid or sulfamic acid may also be employed. In one embodiment, the aliphatic compound is sulfonated with sulfur trioxide diluted with air. The charge mole ratio of sulfur trioxide to alkylate is maintained at about 0.8 to about 1.1:1.

If desired, neutralization of the aliphatic sulfonic acid may be carried out in a continuous or batch process by any method known to a person skilled in the art to produce aliphatic sulfonates. Typically, an aliphatic sulfonic acid is neutralized with a source of alkali or alkaline earth metal or ammonia, thereby producing an aliphatic sulfonate. In one embodiment, the source is an alkali metal base such as sodium hydroxide or potassium hydroxide.

In one embodiment, the one or more asphaltene modifiers is one or more alkyl-substituted hydroxyaromatic carboxylic acids or salts thereof. Suitable hydroxyaromatic compounds include single ring, double ring or fused ring hydroxyaromatic compounds. In one embodiment, suitable hydroxyaromatic compounds include mononuclear monohydroxy and polyhydroxy aromatic hydrocarbons having 1 to 4, and preferably 1 to 3, hydroxyl groups. Representative examples of hydroxyaromatic compounds include phenol, catechol, resorcinol, hydroquinone, pyrogallol, cresol, and the like. The preferred hydroxyaromatic compound is phenol.

In one embodiment, the alkyl substituted moiety of the alkyl-substituted hydroxyaromatic carboxylic acid or salt thereof can be a branched chain alkyl group containing from about 10 carbon atoms to about 80 carbon atoms or linear chain alkyl group containing 10 carbon atoms to 80 carbon atoms, or mixtures thereof. In one embodiment, the alkyl substituted moiety of the alkyl-substituted hydroxyaromatic carboxylic acid or salt thereof can be a branched chain alkyl group containing from about 20 carbon atoms to about 60 carbon atoms or linear chain alkyl group containing 20 carbon atoms to 60 carbon atoms, or mixtures thereof. In one embodiment, the alkyl substituted moiety of the alkyl-substituted hydroxyaromatic carboxylic acid or salt thereof can be a 50:50 weight percent mixture of branched chain alkyl group containing about 8 carbon atoms to about 20 carbon atoms and linear chain alkyl group containing from about 20 carbon atoms to about 30 carbon atoms. The linear chain alkyl group and the branched chain alkyl group is independently attached to the hydroxyaromatic compound such as hydroxybenzene in a position ortho or para to the hydroxyl group on the benzene moiety.

In one embodiment, the ratio of the attachment of the linear chain alkyl group in the ortho-position to para-position is 70:30 based on the total alkyl-substituted hydroxyaromatic carboxylic acid or salt thereof. In one embodiment, the ratio of the attachment of the linear chain alkyl group in the ortho-position to para-position is 60:40 based on the total alkyl-substituted hydroxyaromatic carboxylic acid or salt thereof. In another embodiment, the ratio of the attachment of the branched chain alkyl group in the ortho-position to para-position is 20:80 based on the total alkyl-substituted hydroxyaromatic carboxylic acid or salt thereof. In another embodiment, the ratio of the attachment of the branched chain alkyl group in the ortho-position to para-position is 5:95 based on the total alkyl-substituted hydroxyaromatic carboxylic acid or salt thereof.

In one embodiment, the alkyl substituted moiety of the alkyl-substituted hydroxyaromatic carboxylic acid or salt thereof can be derived from an alpha olefin having from about 10 to about 80 carbon atoms. In one embodiment, the alkyl substituted moiety of the alkyl-substituted hydroxyaromatic carboxylic acid or salt thereof can be derived from an alpha olefin having from about 20 to about 60 carbon atoms. The olefins employed may be linear, isomerized linear, branched or partially branched linear. The olefin may be a mixture of linear olefins, a mixture of isomerized linear olefins, a mixture of branched olefins, a mixture of partially branched linear or a mixture of any of the foregoing.

In one embodiment, the mixture of linear olefins that may be used is a mixture of normal alpha olefins selected from olefins having from about 12 to about 30 carbon atoms per molecule. In one embodiment, the normal alpha olefins are isomerized using at least one of a solid or liquid catalyst.

In another embodiment, the olefins are a branched olefinic propylene oligomer or mixture thereof having from about 20 to about 80 carbon atoms, i.e., branched chain olefins derived from the polymerization of propylene. The olefins may also be substituted with other functional groups, such as hydroxy groups, carboxylic acid groups, heteroatoms, and the like. In one embodiment, the branched olefinic propylene oligomer or mixtures thereof have from about 20 to about 60 carbon atoms. In one embodiment, the branched olefinic propylene oligomer or mixtures thereof have from about 20 to about 40 carbon atoms.

In one embodiment, at least about 75 mole % (e.g., at least about 80 mole %, at least about 85 mole %, at least about 90 mole %, at least about 95 mole %, or at least about 99 mole %) of the alkyl groups contained within the alkyl-substituted hydroxyaromatic carboxylic acid are a $C_{20}$ or higher. In another embodiment, the alkyl-substituted hydroxyaromatic carboxylic acid or salt thereof is an alkyl-substituted hydroxybenzoic acid or salt thereof that is derived from an alkyl-substituted hydroxybenzoic acid in which the alkyl groups are the residue of normal alpha-olefins containing at least 75 mole % $C_{20}$ or higher normal alpha-olefins.

In another embodiment, at least about 50 mole % (e.g., at least about 60 mole %, at least about 70 mole %, at least about 80 mole %, at least about 85 mole %, at least about 90 mole %, at least about 95 mole %, or at least about 99 mole %) of the alkyl groups contained within alkyl-substituted hydroxyaromatic carboxylic acid or salt thereof are about $C_{14}$ to about $C_{18}$.

The carboxylic acid moiety on the alkyl-substituted hydroxyaromatic carboxylic acid may be attached directly or indirectly to the alkyl-substituted hydroxyaromatic compound. In one preferred embodiment, the carboxylic acid moiety is attached directly to the alkyl-substituted hydroxyaromatic compound.

Suitable salts of the alkyl-substituted hydroxyaromatic carboxylic acid include alkali or alkaline earth metal salts of an alkyl-substituted hydroxyaromatic carboxylic acid. Non-limiting examples of suitable alkali metals and alkaline earth metals include those discussed hereinabove.

The method for preparation of the alkyl-substituted hydroxyaromatic carboxylic acid is well known in the art. Generally, the alkyl-substituted hydroxyaromatic carboxylic acid is prepared by carboxylation of the corresponding alkyl-substituted hydroxyaromatic compounds using carbon dioxide. The metal salts are prepared using the oxides, hydroxide or alkoxides of the desired metal. For example, the alkyl-substituted hydroxyaromatic carboxylic acids may be prepared as described in U.S. Pat. No. 6,162,770.

The alkali or alkaline earth metal salts of an alkyl-substituted hydroxyaromatic carboxylic acid can be neutral or overbased. Generally, an overbased alkali or alkaline earth metal salt of an alkyl-substituted hydroxyaromatic carboxylic acid is one in which the BN of the alkali or alkaline earth metal salts of an alkyl-substituted hydroxyaromatic carboxylic acid has been increased by a process such as the addition of a base source (e.g., lime) and an acidic overbasing compound (e.g., carbon dioxide). Methods for overbasing are well known in the art.

In general, the one or more asphaltene modifiers can be added to the blend in an amount ranging from about 10 ppm to about 3 wt. %, based on the total weight of the blend. In one embodiment, the one or more asphaltene modifiers can be added to the blend in an amount ranging from about 50 ppm to about 1000 ppm, based on the total weight of the blend.

In order to transport the resulting liquid crude hydrocarbon composition, a blend comprising (i) one or more hydrocarbon-containing solvent having an aromatic content of at least about 10 wt. %; and (ii) one or more asphaltene modifiers selected from the group consisting of an aromatic sulfonic acid or salt thereof, an aliphatic sulfonic acid or salt thereof and an alkyl-substituted hydroxyaromatic carboxylic acid or salt thereof, is first prepared prior to its addition to the liquid crude hydrocarbon having an API gravity of less than or equal to about 20. The blend is formed by simply blending or mixing the one or more hydrocarbon-containing solvents with the one or more asphaltene modifiers by any known blending or mixing technique. Once the blend is formed, a minor amount of it is then added to the liquid crude hydrocarbon to form the liquid crude hydrocarbon composition. The liquid crude hydrocarbon composition is then ready to be transported by way of a pipeline to a desired location such as a treatment facility or to a transportation carrier such as, for example, a railroad, truck, or ship in, for example, containers that include tanks, vessels, and containerized units. The desired location can be a treatment facility such as a refinery where the liquid crude hydrocarbon composition is further processed. In one embodiment, the blend is further processed as is upon reaching its desired location.

In another embodiment, the blend is separated from the liquid crude hydrocarbon composition and then recycled or reused. The separated liquid crude hydrocarbon can be sent to a solvent deasphalting unit to separate the asphaltene fraction and a deasphalted oil fraction essentially free of asphaltenes. The term "essentially free" as used herein shall be understood to mean trace amounts, if any, of that component, e.g., an amount less than about 0.1 weight percent of that component. The asphaltene fraction can be sent to hydroprocessing unit or to a refinery coker unit (e.g., delayed coking or fluidized coking unit) in which the asphaltenes can be further processed into lighter hydrocarbons and petroleum coke.

In yet another embodiment, the separated deasphalted oil fraction can be subjected to further processing. Examples of further processing include using the product as a refinery feedstock in one or more crude hydrocarbon refining components within a refinery and subjected to one or more conventional hydroprocessing techniques such as hydrotreating, hydrocracking, hydrogenation, hydrofinishing and hydroisomerization and the like. Alternatively, one or more of the products can be blended with one or more different hydrocarbon-containing feedstocks. The refinery hydroprocesses that the one or more of the selected hydrocarbon-containing feedstocks can be used in are well known in the art.

The term "crude hydrocarbon refinery component" generally refers to an apparatus or instrumentality of a process to refine crude hydrocarbons, such as an oil refinery process. Crude hydrocarbon refinery components include, but are not limited to, heat transfer components such as a heat exchanger, a furnace, a crude preheater, a coker preheater, or any other heaters, a FCC slurry bottom, a debutanizer exchanger/tower, other feed/effluent exchangers and furnace air preheaters in refinery facilities, flare compressor components in refinery facilities and steam cracker/reformer tubes in petrochemical facilities. Crude hydrocarbon refinery components can also include other instrumentalities in which heat transfer may take place, such as a fractionation or distillation column, a scrubber, a reactor, a liquid-jacketed tank, a pipestill, a coker and a visbreaker. It is understood that "crude hydrocarbon refinery components," as used herein, encompass tubes, piping, baffles and other process transport mechanisms that are internal to, at least partially constitute, and/or are in direct fluid communication with, any one of the above-mentioned crude hydrocarbon refinery components.

In another embodiment, once the liquid crude hydrocarbon composition has been formed, the liquid crude hydrocarbon composition is first transported by way of, for example, a pipeline, and then further transported by another transportation carrier to a desired location such as a refinery for further processing as described hereinabove. For example, the liquid crude hydrocarbon composition can be transported through a pipeline to a ship terminal where the liquid crude hydrocarbon composition is then further transported on a ship to a desired refinery.

The following non-limiting examples are illustrative of the present invention.

EXAMPLE 1

Preparation of $C_{20}$ to $C_{24}$ Isomerized Alpha Olefin (IAO).

The primary olefinic species in Normal Alpha Olefins (NAOs) is typically alpha-olefin. The isomerization of NAOs over a solid acid extrudate catalyst, ICR 502 (purchased from Chevron Lummus Global), isomerizes the alpha-olefin to other olefinic species, such as beta-olefins, internal olefins and even tri-substituted olefins. The isomerization of NAOs over ICR 502 catalyst also induces skeletal isomerization in which methyl groups are introduced along the hydrocarbon chain of the isomerized alpha olefin (IAO) which is referred to as branching. Both the alpha-olefin and branching content of IAOs is conviently monitored by Infrared spectrometry (see Example 2). The degree of olefin and skeletal isomerization of an NAO depends on the conditions of the isomerization process.

In this example, a $C_{20}$ to $C_{24}$ NAO, obtained from Chevron Phillips Chemical Company, was isomerized in a tubular fixed bed reactor (2.54 cm ID×54 cm Length Stainless Steel) packed sequentially from the bottom of the reactor to the top of the reactor as follows: 145 grams Alundum 24, 40 grams of ICR 505 mixed with 85 grams of Alundum 100, and 134 grams of Alundum 24. The reactor was mounted vertically in a temperature controlled electric furnace. The catalyst was dried at approximately 150° C. in a downflow of dry nitrogen of approximately 30 ml/minute. The NAO (heated to approximately 35° C.) was pumped upflow at a WHSV (Weight Hourly Space Velocity) of 1.5 while the catalyst bed was held at temperatures ranging between 130° C. and 230° C. at atmospheric pressure. The IAO collected between 170 and 187° C. showed 64.8% branching and 0.3 wt. % alpha olefin remaining.

EXAMPLE 2

Measurement of % Branching and % Alpha-Olefin in $C_{20}$ to $C_{24}$ Isomerized Alpha Olefin (IAO).

Infrared spectrometry was used to determine the percentage methyl branching and percentage residual alpha-olefin of isomerized $C_{20}$ to $C_{24}$ NAO, i.e., IAO, obtained in Example 1. The technique involves developing a calibration curve between the infrared absorption at 1378 cm$^{-1}$ (characteristic of the methyl stretch) measured by attenuated reflectance (ATR) infrared spectrometry and the percent branching determined by GLPC (Gas Liquid Phase Chromatography) analysis of the corresponding hydrogenated IAO samples (hydrogenation converts the IAO to a mixture of paraffins in which the normal paraffin has the longest GLPC retention time for a give carbon number). Similarly, a calibration curve was developed between the infrared absorption at 907 cm$^{-1}$ (characteristic of alpha olefin C—H stretch) determined by attenuated reflectance (ATR) infrared spectrometry and the percent alpha-olefin determined by quantitative carbon NMR.

A linear least squares fit of data for the percent branching showed the following equation:

% Branching by Hydrogenation GC=3.0658×(Peak Height at 1378 cm$^{-1}$, in mm, by ATR Infrared Spectroscopy)−54.679.

The correlation coefficient (R2), which is generally used as a measure of how well the regression equation fits the raw data, was 0.9321 and the branching content of the samples used to generate this calibration equation ranged from approximately 9% to 92%.

Similarly, a linear least squares fit of the percent alpha-olefin data showed the following equation:

% Alpha-Olefin by Carbon NMR=0.5082×(Peak Height at 909 cm−1, in mm, by ATR Infrared Spectroscopy)−2.371.

The correlation coefficient (R2) was 0.9884 and the alpha-olefin content of the samples used to generate this calibration equation ranged from approximately 1% to 75%.

EXAMPLE 3

Sulfonation of 64.8% Branched $C_{20}$ to $C_{24}$ IAO.

A sample of the 64.8% branched $C_{20}$ to $C_{24}$ IAO from Example 1 (containing 0.3 wt. % residual alpha olefin) was sulfonated in a glass, water jacketed, falling film tubular reactor (0.6 cm ID and three reactors in series, R1=30 cm, R2=30 cm and R3=70 cm) using SO3/Air and the following conditions:

IAO Feed Temperature=35° C.
Reactor Temperature=30° C.
Air Flow=192 liters/hr
$SO_2$ Flow=16 liters/hr
$SO_2$ to $SO_3$ conversion=87%
IAO Feed Rate=4.0 grams/minute The resulting crude $C_{20}$ to $C_{24}$ isomerized olefin sulfonic acid was then digested at 40° C. for 20 minutes in air to afford the following sulfonic acid: 64.4 wt % $RSO_3H$ and 1.85 wt. % $H_2SO_4$ by cyclohexylamine titration.

EXAMPLE 4

Preparation of $C_{20}$ to $C_{28}$ Alkyl-Substituted Hydroxyaromatic Carboxylic Acid.

The preparation of $C_{20}$ to $C_{28}$ alkyl substituted hydroxyaromatic carboxylic acid involves three steps starting from $C_{20}$ to $C_{28}$ alkylphenol (OLOA 200H, commercially available from Chevron Oronite Company LLC): Step I—Neutralization, Step II—Carboxylation and Step III—Acidification.

Step I—Neutralization of $C_{20}$ to $C_{28}$ Alkylphenol to Prepare the Corresponding Potassium Salt A commercial $C_{20}$ to $C_{28}$ alkylphenol (OLOA 200 H) made from a mixture of unisomerized $C_{20}$ to $C_{24}/C_{26}$ to $C_{28}$ NAO (80:20) obtained from Chevron Phillips Chemical Company with the following properties: 1.0% Ether, 3.5% Di-alkylate, 35.9% Para-alkyl-isomer, 0.8% free phenol and 0.8% Unreacted olefin/paraffin by HPLC.9415), (1500 grams, 3.70 moles) was charged to a 4 liter round bottom, four neck flask equipped with a Dean Stark trap and condenser followed by 750 grams of mixed xylenes and 0.2 grams of foam inhibitor. The mixture was heated to 60° C. over 15 minutes with agitation and then 444.0 grams (3.43 moles corrected for purity) of 50 wt % aqueous KOH solution was added over 10 minutes. This mixture was then heated to 135° C. over 150 minutes. At the beginning of this temperature ramp to 135° C., the pressure was reduced to 450 mm Hg. The resulting refluxing xylenes were maintained at reflux for an additional 3 hours at which point about 300 ml of water was recovered from the Dean Stark trap. The reaction was then cooled to room temperature and kept under an atmosphere of dry nitrogen to obtain a potassium alkylphenol salt/xylene solution. Analysis of this liquid showed the presence of water=200 ppm and Total Base Number=82.0.

Step II—Carboxylation of the Potassium Salt of $C_{20}$ to $C_{28}$ Alkylphenol.

The potassium alkylphenol salt/xylene solution obtained from Step I was heated to 100° C. and transferred to a 4 liter stainless steel pressure reactor. The contents of the reactor were heated to 140° C. and $CO_2$ was bubbled through the product until the reactor reached 3 bar of pressure. The reaction was held at 140° C. and a constant pressure of 3 bar of $CO_2$ for 4 hours. The contents of the reactor were cooled to approximately 100° C. to afford a xylene solution of the potassium carboxylate with the following properties: 32.0% xylene by mass balance; Carboxylic Acid=65.0 mg KOH/gram [determined by titration] and Salicylic acid Index=73.0 mg KOH/gram [determined by titration] of sample by titration.

Step III—Acidification of the Potassium Carboxylate Derived from $C_{20}$ to $C_{28}$ Alkylphenol.

The potassium carboxylate/xylene solution (1100 grams) obtained from Step II was poured into a 4 liter, round bottom four neck flask fitted with a mechanical stirrer, reflux condenser, thermometer under a dry nitrogen atmosphere at room temperature followed by 254 gram of mixed xylenes. To this mixture was added 767 grams of 10 wt. % aqueous $H_2SO_4$ over 30 minutes with stirring. During this time, the reaction was heated to 60° C. The product was transferred to a separatory funnel and allowed to stand approximately 2 hours to allow phase separation at which time the organic phase was obtained with the following properties: Carboxylic Acid=41.8 mg KOH/gram and Salicylic Acid Index=48.0 mg KOH/gram of sample by titration; 57.5% xylene by mass balance; Water=3100 ppm; K=116 ppm.

The organic phase was then dried over anhydrous MgSO4, filtered and xylene was removed by distillation under vacuum to afford the final $C_{20}$ to $C_{28}$ alkyl-substituted hydroxyaromatic carboxylic acid.

EXAMPLE 5

Preparation of $C_{18}$ Alkyl-Substituted Ortho-Xylene Sulfonic Acid.

The preparation of the $C_{18}$ alkyl-substituted ortho-xylene sulfonic acid involves two steps: Step I—alkylation of ortho-xylene with 1-octadecene to produce a $C_{18}$ alkyl-substituted ortho-xylene and Step II—sulfonation of the $C_{18}$ alkyl-substituted ortho-xylene.

Step I—Alkylation of Ortho-Xylene with 1-Octadecene.

To a 4 liter, four neck, glass round bottom flask equipped with a mechanical stirrer, reflux condenser and thermometer was added 1038 grams (9.8 moles) of ortho-xylene followed by 52.1 grams (0.39 moles) of solid aluminium trichloride in one portion with stirring under an atmosphere of nitrogen. To this stirring mixture was added 492.5 grams (1.95 moles) of 1-octadecene (obtained from Chevron Phillips Chemical Company) over approximately 30 minutes slowly to maintain the temperature of the reaction between 38 and 44° C. The reaction was cooled to room temperature and quenched by adding 0.1 N aqueous NaOH (the temperature of the reaction increased to 57° C.). The contents of the glass flask were transferred to a separatory funnel and the aqueous layer was separated and the organic layer was washed with 0.1 N aqueous NaOH followed by four washings with 800 ml water. The organic layer was dried over anhydrous MgSO4, filtered and the excess ortho-xylene removed by distillation under vacuum (rotoevaporator) to afford 587 grams of n-$C_{18}$ alkyl ortho-xylene containing approximately 98.6 wt. % mono-alkylate and no detectable 1,2,3-alkylation isomer by IR.

Step II—Sulfonation of $C_{18}$ Alkyl-Substituted Ortho-Xylene.

A sample of the $C_{18}$ alkyl-substituted ortho-xylene from Step I was sulfonated in a glass, water jacketed, falling film tubular reactor (0.6 cm ID and three reactors in series, R1=30 cm, R2=30 cm and R3=70 cm) using $SO_3$/Air and the following conditions:

Alkylate Feed Temperature=65° C.
Reactor Temperature=55° C.
Air Flow=192 liters/hr
$SO_2$ Flow=16 liters/hr
$SO_2$ to $SO_3$ conversion=98%
Alkylate Feed Rate=4.09 gms/minute The resulting crude $C_{18}$ alkyl-substituted ortho-xylene sulfonic acid had the following properties: 75.9 wt. % sulfonic acid and 0.14 wt. % $H_2SO_4$.

EXAMPLES 6-11

Preparation of a Liquid Crude Hydrocarbon Composition.

The properties of an extra heavy crude oil and hydrocarbon-containing solvent used to form a liquid crude hydrocarbon composition are listed in Table 1. The hydrocarbon-containing solvent used had an aromatic content of 23.5 wt. %. As shown in Table 2 below, separate preparations were prepared in which the asphaltene modifier of Example 2 or Example 3 were first dissolved in the hydrocarbon-containing solvent at room temperature to form a blend, which was then slowly added to the extra heavy crude oil and shaken for 1 to 3 hours at room temperature. Viscosity measurements were obtained using ASTM D-445 and are reported as average of at least two determinations with error of ±2%. A control run was performed for each of the examples in which the extra heavy crude oil was added to hydrocarbon-containing solvent in the absence of the asphaltene modifier and their viscosities (in brackets) along with the viscosity of the respective liquid crude hydrocarbon composition are reported in Table 2.

TABLE 1

| Analysis | Extra heavy Crude Oil | Hydrocarbon-Containing Solvent |
| --- | --- | --- |
| API (60/60) | 7.7 | 43.6 |
| Viscosity at 40° C. (cSt) | 65,689 | |
| Viscosity at 60° C. (cSt) | | 1.23 |
| Distillation (% Vol) | | |
| Initial Boiling Point (° F.) | 395 | 219 |
| 5% | 545 | 281 |
| 10% | 624 | 304 |
| 20% | 748 | 334 |
| 30% | 850 | 359 |
| 40% | 958 | 385 |
| 50% | 1071 | 406 |
| 60% | 1183 | 427 |
| 70% | 1346 | 452 |
| 80% | | 478 |
| 90% | | 510 |
| 95% | | 532 |
| Final Boiling Point (° F.) | | 603 |

TABLE 2

| | Ex. 6 | Ex. 7 | Ex. 8 | Ex. 9 | Ex. 10 | Ex. 11 |
| --- | --- | --- | --- | --- | --- | --- |
| Extra heavy Crude Oil, grams | 15.39 | 15.25 | 15.15 | 15.21 | 15.07 | 15.13 |
| Hydrocarbon-Containing Solvent, grams | 5.032 | 5.028 | 5.008 | 4.9989 | 5.0022 | 5.0188 |
| Asphaltene Modifier of Example 2, grams | 0.6002 | 0.099 | 0.0211 | | | |
| Asphaltene Modifier of Example 3, grams | | | | 0.6097 | 0.1069 | 0.0245 |
| Viscosity at 40° C. | 224.9 | 228.5 | 215.2 | 158.9 | 219.5 | 239.8 |
| (Control run) | (262.0) | (244.0) | (250.7) | (234.4) | (239.0) | (253.8) |

EXAMPLE 12

Evaluating the Effect of the Asphaltene Modifiers at High Concentrations.

In order to evaluate the effect of the asphaltene modifiers, viscosity reductions for the extra heavy crude oil/blends prepared according to Example 5 were calculated using equation (1):

$$\% \ Red \ Vis = \frac{(Vis_b - Vis_o)}{Vis_o} \times 100 \qquad (1)$$

where $Vis_b$ is the viscosity of the liquid crude hydrocarbon composition containing the extra heavy crude oil and hydrocarbon-containing solvent/asphaltene modifier blend at 40° C. and $Vis_o$ is the viscosity of a control sample containing the extra heavy crude oil and hydrocarbon-containing solvent in the absence of an asphaltene modifier at 40° C.

As can be seen in FIG. 1, a reduction in the viscosity of the liquid crude hydrocarbon composition containing the extra heavy crude oil and hydrocarbon-containing solvent/asphaltene modifier blend was observed for the two different asphaltene modifiers used. The viscosity reductions are significant and well above the error of the technique (±2%). The largest reduction was observed to occur at the highest concentration for the two asphaltene modifiers. However, there is also a significant reduction in the viscosity (almost 10 to 15%) at low concentration (<0.5 wt. % or 5000 ppm). Since a good efficiency at low concentration is fundamental, the performance of some of the asphaltene modifiers at low concentrations was studied.

EXAMPLES 13-18

Evaluating the Effect of the Asphaltene Modifiers at Low Concentration.

As shown in Table 3, separate preparations of liquid crude hydrocarbon compositions containing the extra heavy crude oil and hydrocarbon-containing solvent/asphaltene modifier blend were prepared in substantially the same manner as in Examples 6-11 except that the asphaltene modifiers obtained in Example 2 and Example 3 were used in a concentration of 100 ppm, 400 ppm and 1000 ppm. A control run was also performed for each of the examples in which the extra heavy crude oil was added to the hydrocarbon-containing solvent in the absence of the asphaltene modifier, and their viscosities (in brackets) along with the viscosity of the respective liquid crude hydrocarbon composition are reported in Table 3.

TABLE 3

| | Ex. 13 | Ex. 14 | Ex. 15 | Ex. 16 | Ex. 17 | Ex. 18 |
|---|---|---|---|---|---|---|
| Extra heavy Crude Oil, grams | 15.13 | 15.12 | 15.37 | 15.45 | 15.34 | 15.11 |
| Hydrocarbon-Containing Solvent, grams | 5.0269 | 5.0151 | 5.0001 | 5.0056 | 5.0322 | 4.5053 |
| Asphaltene Modifier of Example 2, grams | 0.0205 (1000 ppm) | 0.0082 (400 ppm) | 0.0020 (100 ppm) | | | |
| Asphaltene Modifier of Example 3, grams | | | | 0.0204 (1000 ppm) | 0.0082 (400 ppm) | 0.0020 (100 ppm) |
| Viscosity at 40° C. (Control run) | 126.8 (143.2) | 127.8 (143.4) | 122.9 (147.8) | 143.2 (148.4) | 119.0 (147.1) | 142.7 (190.1) |

Figure 2:
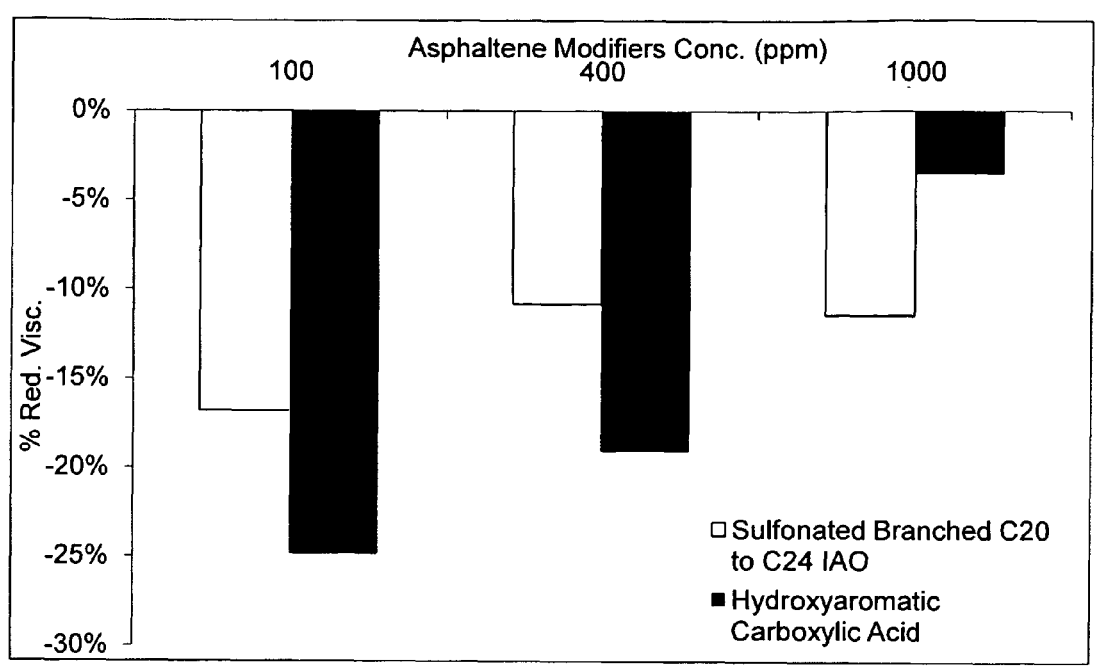
FIG. 2 shows viscosity reduction at a low concentration of asphaltene modifier in a liquid crude hydrocarbon composition containing a 75/25 wt. % ratio of an extra heavy crude oil and hydrocarbon-containing solvent/asphaltene modifier blend, respectively.

As can be seen in FIG. 2, a viscosity reduction was observed for all the blends. The highest viscosity reduction was observed for the lowest asphaltene modifiers concentration. These results are of particular importance because dosage of the asphaltene modifier is a key aspect in determining the economical success so the high activity shown by these modifiers at low concentration demonstrates the potentiality of this route in the transportation of an extra heavy crude oil.

The reduction of viscosity achieved using small amounts of the asphaltene modifier is quite unexpected. In fact, the results obtained indicate that there is an increase in the activity of the asphaltene modifier (larger viscosity reduction) as its concentration decreases. It is believed that it is a result of the colloidal behavior of the asphaltene modifier. At low concentrations, these compounds remained dispersed in the fluid and can interact with the asphaltenes thereby preventing their association, decreasing the colloidal interactions and, therefore decreasing the viscosity.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A liquid crude hydrocarbon composition comprising:
   (a) a liquid crude hydrocarbon having an API gravity of less than or equal to about 20; and
   (b) a minor amount of a blend comprising (i) one or more hydrocarbon-containing solvents having an aromatic content of at least about 20 wt. %; and (ii) one or more asphaltene modifiers which are one or more branched $C_8$ to $C_{60}$ olefin sulfonic acids or salts thereof prepared by sulfonating an isomerized $C_8$ to $C_{60}$ olefin; wherein the one or more asphaltene modifiers are present in an amount ranging from about 50 ppm to 400 ppm, based on the total weight of the blend.

2. The liquid crude hydrocarbon composition of claim 1, wherein the liquid crude hydrocarbon having an API gravity of less than or equal to about 20 comprises a heavy crude oil.

3. The liquid crude hydrocarbon composition of claim 1, wherein the liquid crude hydrocarbon having an API gravity of less than or equal to about 20 comprises an extra heavy crude oil.

4. The liquid crude hydrocarbon composition of claim 1, wherein the liquid crude hydrocarbon having an API gravity of less than or equal to about 20 has a viscosity greater than about 100 cSt and no more than 2,000,000 cSt at 40° C.

5. The liquid crude hydrocarbon composition of claim 1, wherein the one or more hydrocarbon-containing solvents comprises an aromatic refinery stream solvent.

6. The liquid crude hydrocarbon composition of claim 1, wherein the minor amount of the blend is from about 10 wt. % to about 40 wt. %, based on the total weight of the liquid crude hydrocarbon composition.

7. The liquid crude hydrocarbon composition of claim 1, wherein the minor amount of the blend is from about 15 wt. % to about 35 wt. %, based on the total weight of the liquid crude hydrocarbon composition.

8. The liquid crude hydrocarbon composition of claim 1, wherein the one or more asphaltene modifiers which are one or more branched $C_{10}$ to $C_{50}$ olefin sulfonic acids or salts thereof prepared by sulfonating an isomerized $C_{10}$ to $C_{50}$ olefin.

9. The liquid crude hydrocarbon composition of claim 1, wherein the one or more asphaltene modifiers which are one or more branched $C_{12}$ to $C_{40}$ olefin sulfonic acids or salts thereof prepared by sulfonating an isomerized $C_{12}$ to $C_{40}$ olefin.

10. The liquid crude hydrocarbon composition of claim 1, wherein the one or more asphaltene modifiers which are one or more branched $C_{18}$ to $C_{28}$ olefin sulfonic acids or salts thereof prepared by sulfonating an isomerized $C^{18}$ to $C_{28}$ olefin.

* * * * *